(12) United States Patent
Contag

(10) Patent No.: US 8,986,962 B2
(45) Date of Patent: Mar. 24, 2015

(54) ORGANISM CO-CULTURE IN THE PRODUCTION OF BIOFUELS

(76) Inventor: Pamela R. Contag, San Jose, CA (US)

(*) Notice: Subject to any disclaimer, the term of this patent is extended or adjusted under 35 U.S.C. 154(b) by 128 days.

(21) Appl. No.: 13/187,907

(22) Filed: Jul. 21, 2011

(65) Prior Publication Data
US 2012/0124898 A1    May 24, 2012

Related U.S. Application Data

(60) Provisional application No. 61/366,283, filed on Jul. 21, 2010.

(51) Int. Cl.
| | | |
|---|---|---|
| C12P 7/02 | (2006.01) | |
| C12P 7/06 | (2006.01) | |
| C12P 7/14 | (2006.01) | |
| C12P 7/16 | (2006.01) | |
| C12N 11/00 | (2006.01) | |
| C12N 11/16 | (2006.01) | |
| C12P 39/00 | (2006.01) | |
| C12N 1/12 | (2006.01) | |
| C12P 7/64 | (2006.01) | |

(52) U.S. Cl.
CPC . *C12P 39/00* (2013.01); *C12N 1/12* (2013.01); *C12P 7/06* (2013.01); *C12P 7/16* (2013.01); *C12P 7/6463* (2013.01); *Y02E 50/10* (2013.01); *Y02E 50/17* (2013.01); *Y02E 50/343* (2013.01)
USPC .......... 435/155; 435/160; 435/161; 435/162; 435/174; 44/436; 44/451

(58) Field of Classification Search
None
See application file for complete search history.

(56) References Cited

U.S. PATENT DOCUMENTS

| | | | |
|---|---|---|---|
| 2008/0293086 A1 | 11/2008 | Contag | |
| 2009/0017512 A1* | 1/2009 | May et al. | 435/165 |
| 2010/0151540 A1 | 6/2010 | Gordon | |
| 2010/0159567 A1 | 6/2010 | Kuehnle | |
| 2011/0045528 A1 | 2/2011 | Dhamwichukorn | |

FOREIGN PATENT DOCUMENTS

| | | | | |
|---|---|---|---|---|
| WO | 2009105733 A2 | 8/2009 | | |
| WO | WO2009/111513 | * 9/2009 | .............. | C12M 1/00 |
| WO | 2010044960 A1 | 4/2010 | | |

OTHER PUBLICATIONS

U.S. Appl. No. 61/106,543, by Green et al. Oct. 17, 2008, 151 pgs.*
U.S. Appl. No. 61/184,757, (Jun. 5, 2009) by Green et al., 168 pgs.*
U.S. Appl. No. 61/121,532, (Dec. 10, 2008) by Berry et al., 168 pgs.*
"diatomaceous earth (mineralogy)". Encyclopædia Britannica. Encyclopædia Britannica Online. Encyclopædia Britannica Inc., 2013. Web. Aug. 8, 2013 <http://www.britannica.com/EBchecked/topic/161843/diatomaceous-earth>.*
Haug et al. "Polysaccharides of Marine Diatoms with Special Reference to *Chaetoceros* Species" Marine Biology 34, 217-222 (1976).*
George Karleskint "Introduction to Marine Biology", 4th ed. 2013 p. 141.*
Martin-Jézéquel "Silicon Metabolism in Diatoms: Implications for Growth" J. Phycol. 36, 821-840 (2000).*
Pilkington et al. "Fundamentals of Immobilised Yeast Cells for Continuous Beer Fermentation: A Review" J. Inst. Brew., Jan.-Feb. 1998, vol. 104, pp. 19-31.*
PubChem "Silicic Acid-Compound Summary" http://pubchem.ncbi.nlm.nih.gov/summary/summary.cgi?cid=14768 accessed Aug. 8, 2013, 1pg.*
Durkin et al. "Chitin in Diatoms and Its Association with the Cell Wall" Eukaryotic Cell 2009, 8(7):1038.*
Bidle et al. "Accelerated dissolution of diatom silica by marine bacterial assemblages" Nature | vol. 397 | Feb. 11, 1999, pp. 508-512.*
Patrick et al. "The effect of bacteria on the solubilization of silica in diatom frustules" Journal of Applied Bacteriology 1985,59, 7-16.*
Amin et al. "Interactions between Diatoms and Bacteria" Microbiol. Mol. Biol. Rev. 2012, 76(3):667.*
Meunier, C.F. et al., "Encapsulation of cells within silica matrices: Towards a new advance in the conception of living hybrid materials", Journal of Colloid and Interface Science, (2010), pp. 211-224, vol. 342.
Subashchandrabose, S.R. et al., "Consortia of cyanobacteria/microalgae and bacteria: Biotechnological potential", Biotechnology Advances, (2011), pp. 896-907, vol. 29.
Fischer, C.R. et al., "Selection and optimization of microbial hosts for biofuels production", Metabolic Engineering, (2008), pp. 295-304, vol. 10.
Brenner, K. et al., "Engineering microbial consortia: a new frontier in synthetic biology", Trends in Biotechnology, (2008), pp. 483-489, vol. 26.
PCT/US2011/44909—International Search Report and Written Opinion of the International Searching Authority.

* cited by examiner

*Primary Examiner* — Thane Underdahl
(74) *Attorney, Agent, or Firm* — Storella, P.C.

(57) ABSTRACT

This invention provides co-cultures of photosynthetic microorganisms and biofuel producing microorganisms. In certain embodiments, polysaccharide-producing, photosynthetic microorganisms are microalgae having frustules provide a substrate on which biofuel-producing microorganisms can grow. In other embodiments, the photosynthetic microorganisms produce a lipid and the non-photosynthetic microorganisms produce a solvent in which the lipid is soluble.

21 Claims, 6 Drawing Sheets

FIG. 4 Core Technology Based on Photosynthetic Formation of Sugars from Microalgae

*Biomass And Bioreactor In One*

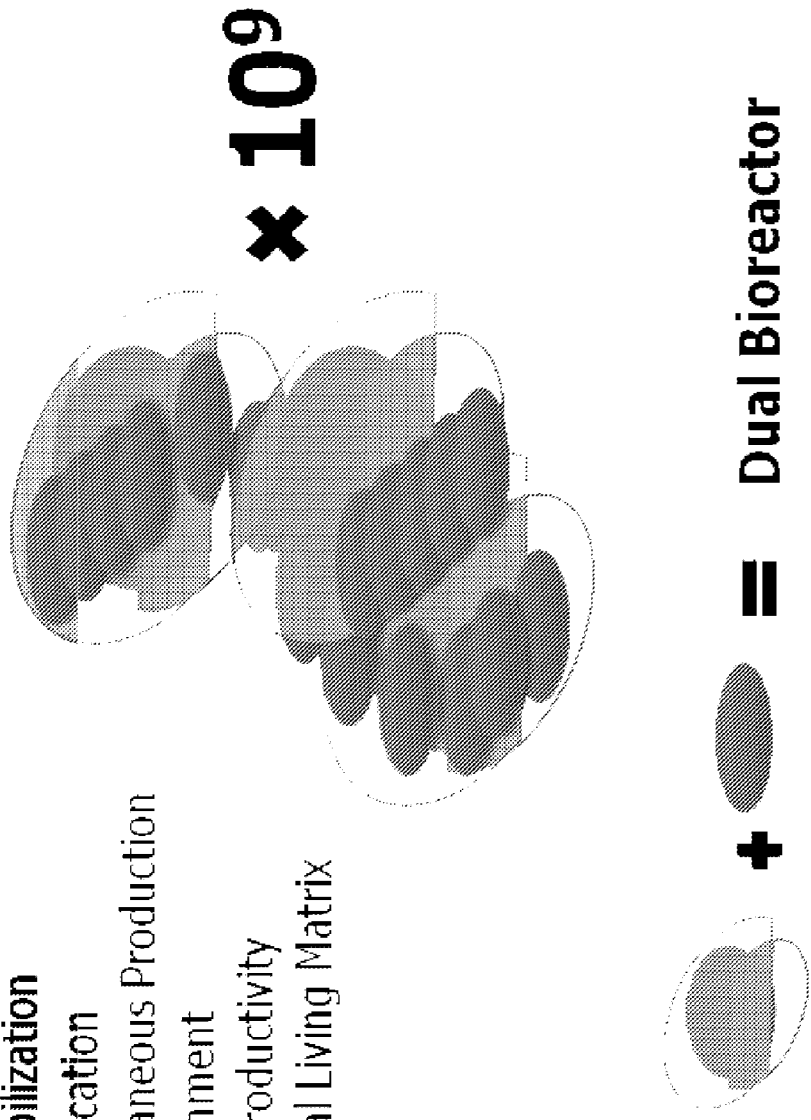

ORGANISM CO-CULTURE IN THE PRODUCTION OF BIOFUELS

CROSS REFERENCE

This application claims the benefit of U.S. Provisional Application Ser. No. 61/366,283, filed Jul. 21, 2010 which application is incorporated herein by reference.

STATEMENT AS TO FEDERALLY SPONSORED RESEARCH

None.

BACKGROUND OF THE INVENTION

Currently, the biofuels industry lacks sufficient renewable feedstocks that are easily fermented to biofuels or new varieties of organisms selected to use diverse feedstock. Current renewable biomass choices include forest waste, switch grass, sorghum, barley, sugar cane and corn. Sources of additional low cost feedstocks are required for the growth of the biofuels industry and to meet governmental goals to replace fossil fuel energy with renewal energy sources.

The current biofuels industry tends to categorize higher plants as feedstock for starch or cellulose, algae as a source of lipids for biodiesel or food oils, and bacteria as fermenting organisms to produce bioalcohols. However, basic science teaches us that algae and bacteria, in addition to higher plants, can be feedstock, degrade feedstock and produce biofuels. Eukaryotic cells are characterized by possessing membrane bound organelles. It is a well-accepted theory (the endosymbiont theory) that these organelles were derived by ancient symbiosis between bacteria, archaea or other eukaryotes. A branch of eukaryotes called the archaeplastida, from which higher plants, algae and glaucophyta are derived, are differentiated from other organisms by the fact that they accumulate starch. Algae obtain energy by photosynthesis, basically producing food (energy) from light. Many algae store energy in the form of starch. For example, red algae store energy in the form of floridean starch, and brown algae store energy as laminarin. *Chlamydomonas*, a eukaryotic, single cell, algae, can grow on inorganic salts in the light, using photosynthesis to provide energy, also stored as starch. They can also grow without light using acetate as a sole carbon source. Recent studies have proven that starch synthesis in Rhodophyceae, Glaucophyta, and Chloroplastida consists of a mosaic of genes that originated from cyanobacterial and eukaryotic glycogen metabolisms, suggesting that endosymbiosis involved partners able to synthesize similar types of storage polysaccharides.

Research at leading universities suggests that algae could supply enough fuel to meet all of America's transportation needs in the form of biodiesel using a scant 0.2% of the nation's land. Enough algae can be grown to replace all transportation fuels in the U.S. on only 15,000 square miles, or 4.5 million acres of land.

SUMMARY OF THE INVENTION

In one aspect this invention provides a method comprising co-culturing polysaccharide-producing photosynthetic microorganisms with polysaccharide-consuming, biofuel-producing, non-photosynthetic microorganisms to produce a biofuel. In one embodiment the photosynthetic microorganisms comprise algae. In another embodiment the co-culturing comprises exposing the photosynthetic microorganisms to light. In another embodiment the non-photosynthetic microorganisms are fermentative. In another embodiment the non-photosynthetic microorganisms comprise bacteria or fungi. In another embodiment the non-photosynthetic microorganisms comprise bacteria selected from *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*. In another embodiment the non-photosynthetic microorganisms comprise fungi selected from *Aspergillus, Candida, Chlamydomonas, Chrysosporium, Cryotococcus, Fusarium, Kluyveromyces, Neotyphodium, Neurospora, Penicillium, Pichia, Saccharomyces, Trichoderma* and *Xanthophyllomyces*. In another embodiment the non-photosynthetic microorganisms are genetically modified to increase biofuel production. In another embodiment the algae comprise diatoms. In another embodiment the diatoms are selected from Coscinodiscophyceae, Fragilariophyceae and Bacillariophyceae. In another embodiment the diatoms are gown with a source of silica. In another embodiment the algae comprise diatoms comprising frustules and wherein the non-photosynthetic microorganisms are immobilized on the frustules. In another embodiment the non-photosynthetic microorganisms comprise yeast. In another embodiment the non-photosynthetic microorganisms comprise *Clostridium*. In another embodiment the biofuel is ethanol, propanol or butanol. In another embodiment the biofuel is an alcohol, an alkene, an alkane, a lipid or a polysaccharide. In another embodiment co-culturing is performed in a bioreactor or in an open environment. In another embodiment wherein co-culturing is performed in an open environment selected from natural waters (e.g., lakes, lagoons or ponds) and artificial ponds. In another embodiment co-culturing is performed in a bioreactor comprising plastic (e.g. polypropylene or an equivalent alternative), steel or glass. In another embodiment the artificial pond is a raceway pond and may have soft sides or hard sides. In another embodiment the method further comprises isolating the biofuel produced by the non-photosynthetic microorganism from the co-culture.

In another aspect this invention provides a method comprising co-culturing a lipid-producing, photosynthetic microorganism with a solvent-producing, non-photosynthetic microorganism, wherein the lipid is soluble in the solvent. In one embodiment the photosynthetic microorganisms comprise algae. In another embodiment the photosynthetic microorganisms comprise cyanobacteria. In another embodiment the photosynthetic microorganisms are selected from, *Botryococcus braunii, Chlorella, Dunaliella tertiolecta, Gracilaria, Pleurochrysis carterae, Sargassum* and *Ulva*. In another embodiment the non-photosynthetic microorganism is *Clostridium*. In another embodiment the solvent is a $C_4$ to $C_{10}$ alcohol. In another embodiment the solvent is butanol. In another embodiment the microorganisms are co-cultured with an external source of carbon. In another embodiment co-culturing is performed in a bioreactor or in an open environment. In another embodiment co-culturing is performed in an open environment selected from natural waters (e.g., lakes, lagoons or ponds) and artificial ponds. In another embodiment the method further comprises liquid-liquid separation of the lipid produced by the photosynthetic microorganism from a medium in which the microorganisms are co-cultured.

In another aspect this invention provides a co-culture of photosynthetic microorganisms and non-photosynthetic organisms wherein the photosynthetic microorganisms produce polysaccharide and the non-photosynthetic microorganisms consume the produced polysaccharide and produce a biofuel.

In one embodiment the photosynthetic microorganisms comprise diatoms. In another embodiment the photosynthetic microorganisms comprise diatoms selected from Coscinodiscophyceae, Fragilariophyceae and Bacillariophyceae. In another embodiment the non-photosynthetic microorganisms are fermentative. In another embodiment the non-photosynthetic microorganisms yeast or *Clostridium*. In another embodiment the non-photosynthetic microorganisms are genetically modified. In another embodiment the biofuel is ethanol, propanol or butanol. In another aspect this invention provides a co-culture of lipid-producing, photosynthetic microorganisms and solvent-producing, non-photosynthetic microorganisms, wherein the lipid is soluble in the solvent. In one embodiment the photosynthetic microorganisms comprise algae. In another embodiment the photosynthetic microorganisms comprise cyanobacteria. In another embodiment the photosynthetic microorganisms are selected from *Botryococcus braunii, Chlorella, Dunaliella tertiolecta, Gracilaria, Pleurochrysis carterae, Sargassum* and *Ulva*. In another embodiment the non-photosynthetic microorganism is *Clostridium*. In another embodiment the solvent is a $C_4$ to $C_{10}$ alcohol. In another embodiment the solvent is butanol. In another the co-culture further comprises an external source of carbon on which the non-photosynthetic microorganisms can grow. In another embodiment the lipid is an oil.

In another aspect this invention provides a composition comprising an oil and an alcohol. In one embodiment the composition further comprises an oxygenation agent. In another embodiment the alcohol comprises butanol. In another embodiment the composition further comprises remnants of algae. In another embodiment the composition further comprises remnants of cyanobacteria.

Incorporation by Reference

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 shows a dual bioreactor. Bioreactor advantages include immobilization, amplification, simultaneous production, containment, high productivity and internal living matrix. Microalgae can be grown to densities of $10^4$ cells/ml to $10^6$ cells/ml, while fermentative microorganisms can be grown to densities of $10^8$ cells/ml to $10^{11}$ cells/ml, e.g., about $10^9$ cells/ml.

DETAILED DESCRIPTION OF THE INVENTION

1. Introduction

Figure 1:
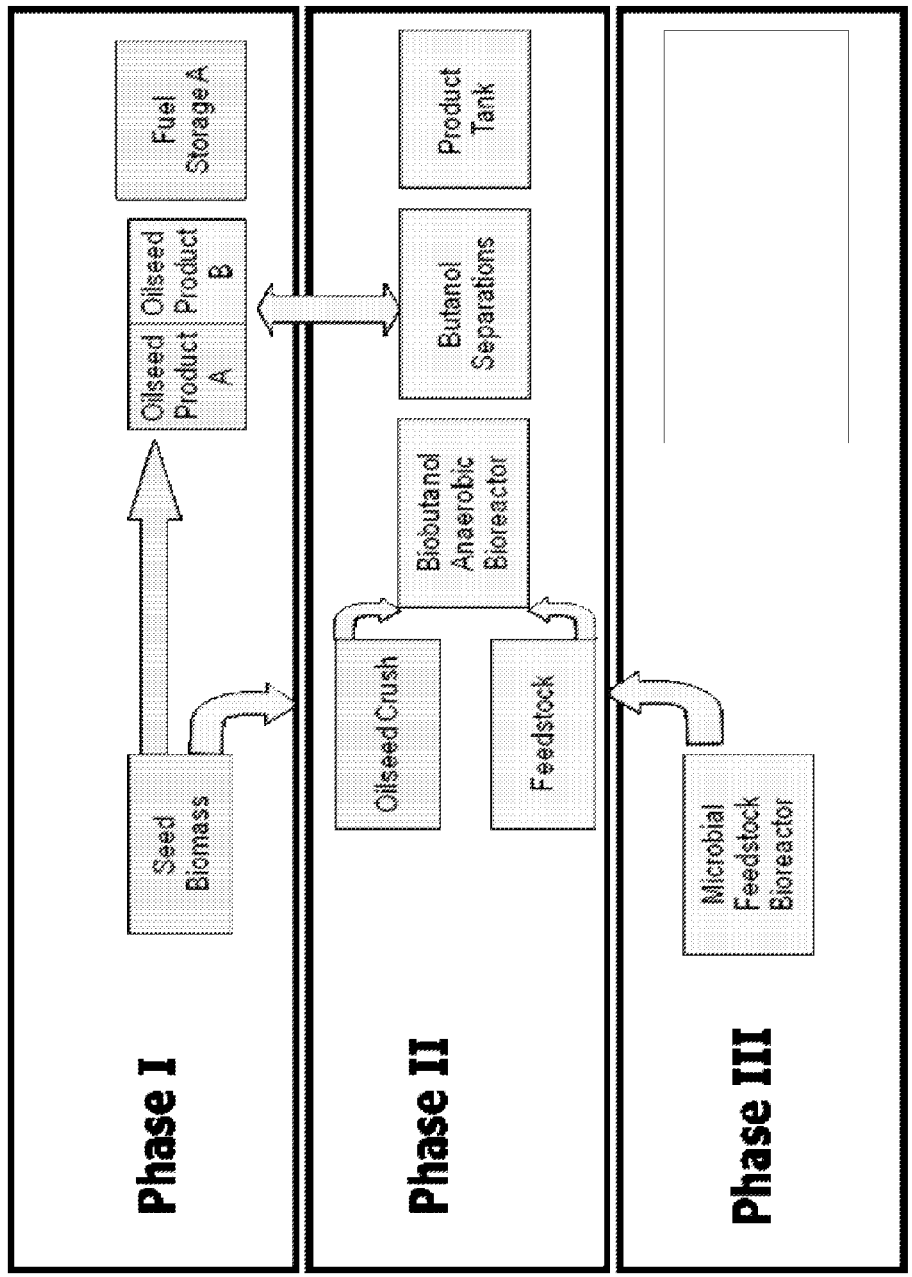
FIG. 1 shows the use of oilseed crush as feedstock for solvent producing bacteria.
Figure 2:
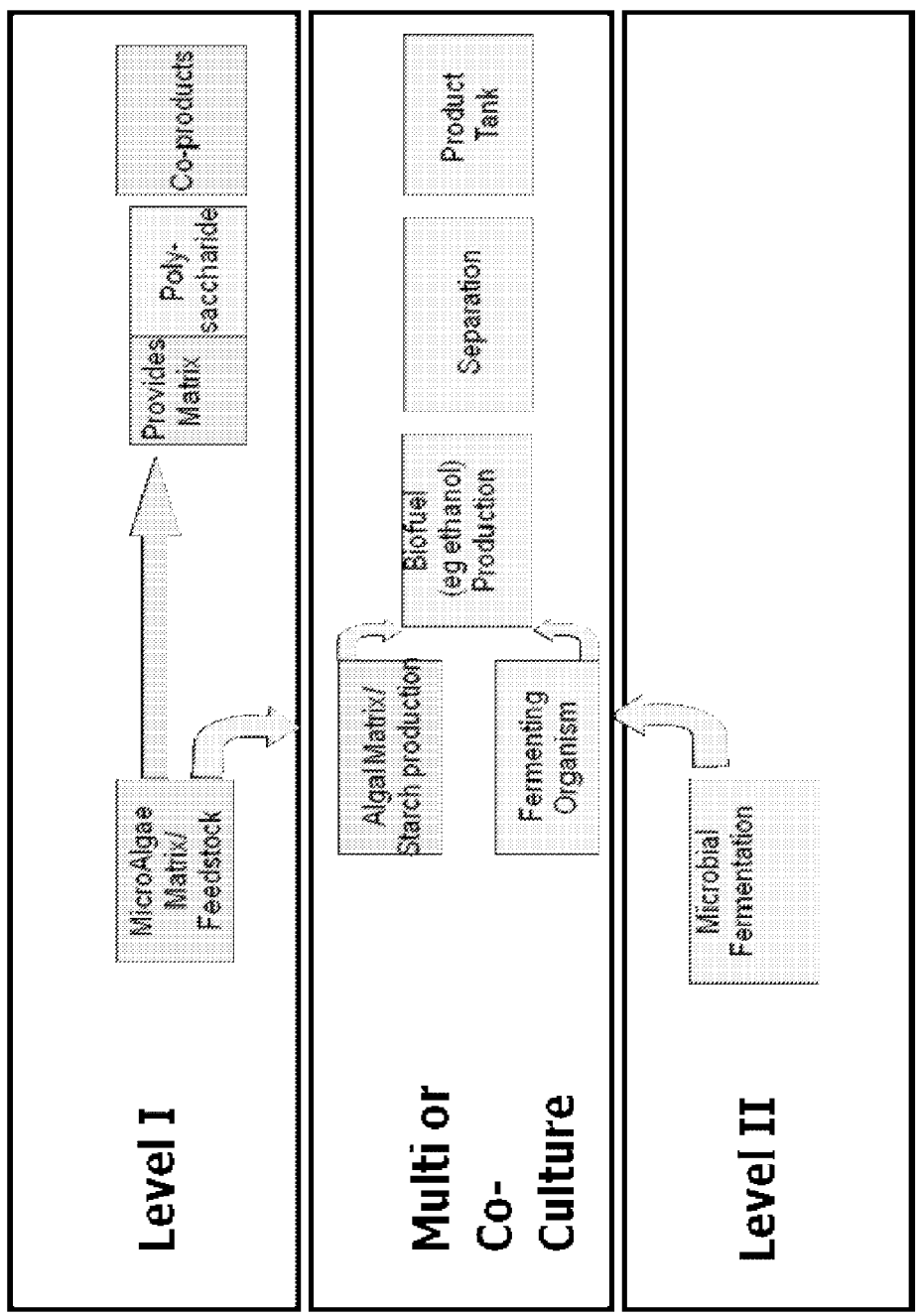
FIG. 2 shows the use of microalgae culture (Level I), co-culture and microbial fermentation (Level II) methods of producing biofuels.
Figure 3:
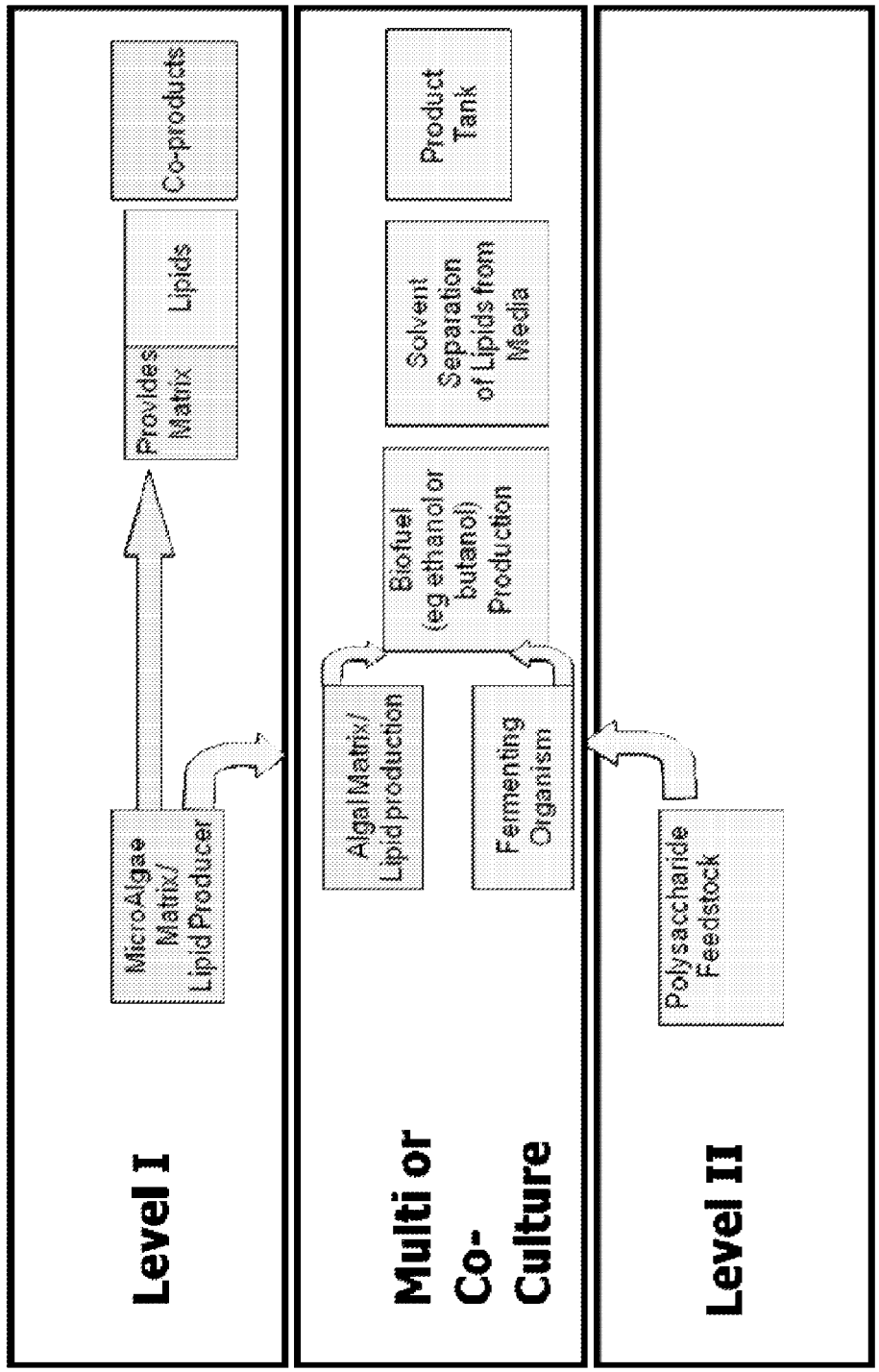
FIG. 3 shows the use of microalgae culture (Level I), co-culture and microbial fermentation (Level II) methods of lipid and solvent production for in situ liquid-liquid separation of biofuel from medium.
Figure 4:
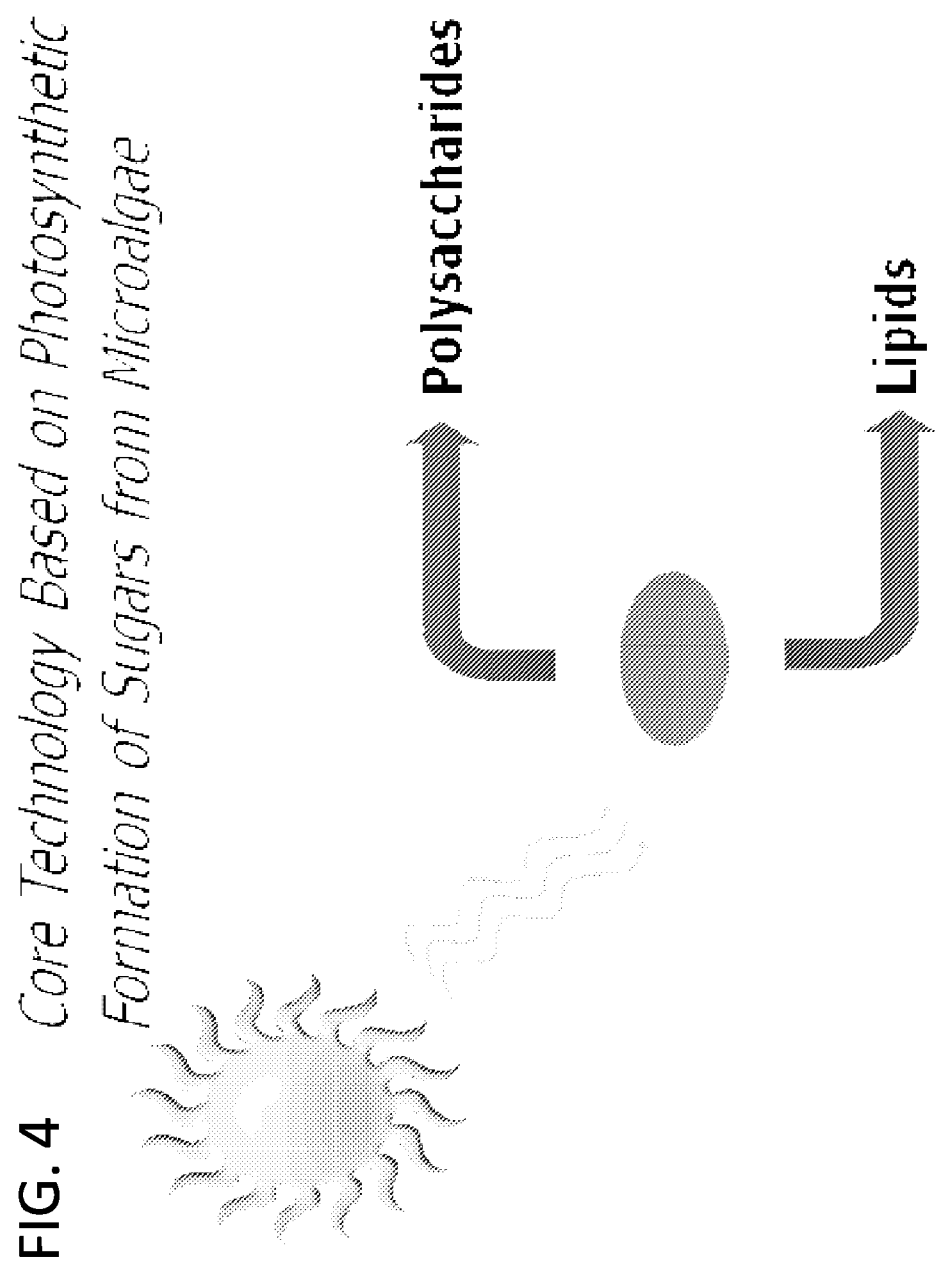
FIG. 4 shows core technology based on photosynthetic formation of sugars from microalgae that can produce polysaccharides and lipids.
Figure 5:
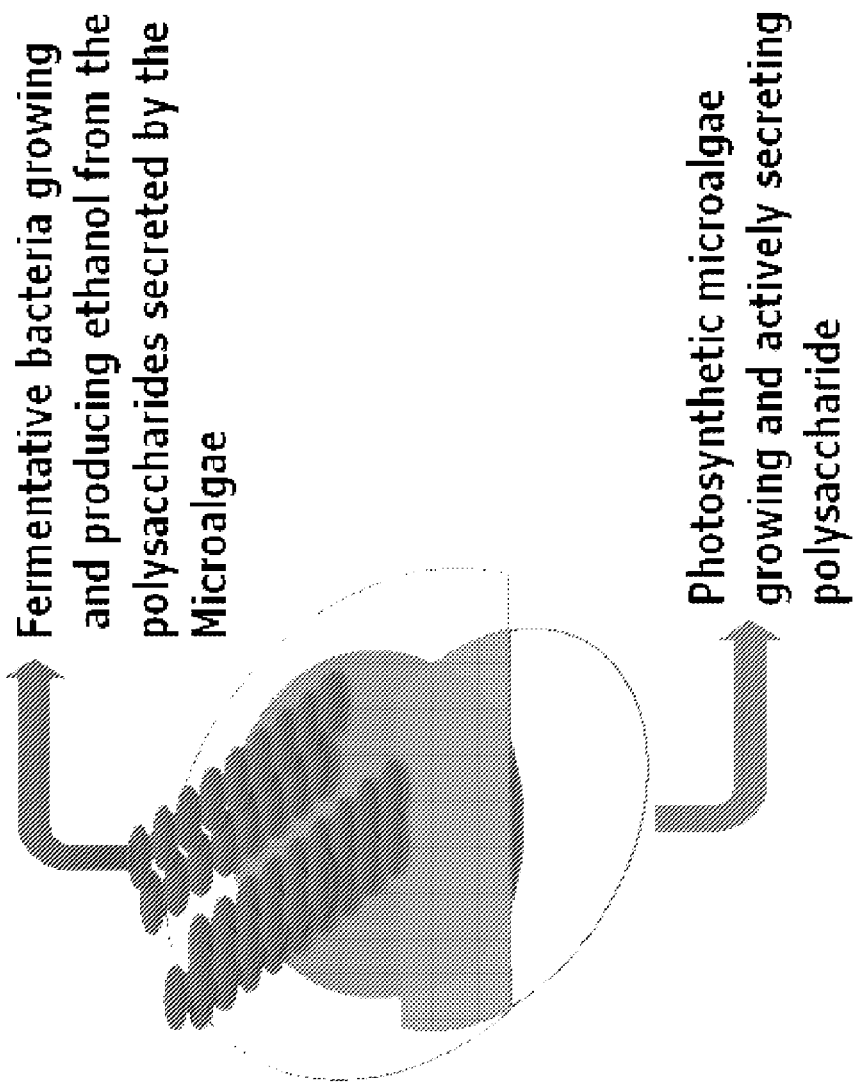
FIG. 5 shows a biomass and bioreactor in one. Photosynthetic microalgae grow and actively secrete polysaccharide. Fermentative bacteria grow and produce ethanol from the polysaccharides secreted by the microalgae.

The invention provides methods of producing biofuel. The methods involve co-culturing different organisms. In certain embodiments, one of the organisms is photosynthetic and the other is non-photosynthetic. In another embodiment, one organism produces a substrate on which a biofuel-producing microorganism can become immobilized. In another embodiment, a one organism, e.g., a photosynthetic organism, e.g., a diatom, produces a carbon source which the biofuel-producing microorganism (e.g., yeast or *Clostridium*) consume. In another embodiment, one organism produces a substrate on which a biofuel-producing microorganism can become immobilized. In particular, one organism can be a unicellular algae, or diatom, that produces a silica substrate. The other microorganism can attach or remain unattached but replicate in the spaces between the diatomaceous matrix or an artificial matrix, such as a filter. In another embodiment, a one organism, e.g., a photosynthetic organism, e.g., a cyanobacterium, produces an oil or lipid, the biofuel-producing microorganism (e.g., *Clostridium*) produces a water insoluble solvent (e.g., butanol) in which the oil or lipid can dissolve, and liquid-liquid extraction is used to separate the oil/solvent mixture from aqueous culture medium.

2. Primary Biofuel-Producing Organisms

The primary biofuel of this invention can be any biofuel. This includes, for example, an alcohol (e.g., methanol, ethanol, propanol, butanol, etc.), a hydrocarbon (e.g., an alkane such methane, ethane, propane, butane, isoprenes, etc.) hydrogen, a biodiesel, an aldehyde or ketones (e.g. acetone, formaldehyde, 1-propanal, etc.). The biofuel can be a solid, a liquid or a gas.

Any biofuel-producing organism can be used in the co-culture of this invention. The organisms can be microorganisms. Organisms can be prokaryotic or eukaryotic. The organisms can be fermentative organisms. Organisms include, for example, *Clostridium* (e.g., *C. acetobutylicum, C. Beijerinckii, C. saccharoperbutylacetonicum, C. saccharobutylicum, C. aurantibutyricum, C. tetanomorphum*), *Zymomonas, Escherichia* (e.g., *E. coli*), *Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula, Zymomonas* and *Saccharomyces*, e.g., *Saccharomyces cerevisiae, Saccharomyces carlsbergensis, Kluyveromyces lactis, Saccharomyces lactis*) In some embodiments, these microorganisms are genetically modified.

Industrially useful microorganisms include the production of ethanol by *Saccharomyces* and the production of butanol by *Clostridium*.

3. Biomass

Highly scaled biorefineries are designed to be capital efficient but require access to large amounts of biomass to be operationally efficient. Crop biomass is the most prevalent biomass and is currently limited by amounts of arable land. Crop biomass includes, for example, corn, switch grass, sugar cane, sugar beet, soybean, sunflower, wood, sorghum, barley and other crops. Biomass diversity is a way to access large total amounts of biomass but requires more capital and operational cost for harvest, transportation and conversion technology.

Photosynthetic unicellular organisms can be a source biomass for biofuel production. Photosynthetic unicellular organisms can yield more biomass per hectare than land plants. Photosynthetic unicellular organisms can produce lipids and starch. The production of lipids and starch from these organisms is specific to their biology. The photosynthetic organism of this invention can be an algae and, in particular, a microalgae, such as a diatom or a cyanobacterium.

Algae.

The high growth rate (biomass yield) and $CO_2$ fixation (photosynthesis) of algae along with their lack of a need to growth on fertile soil (arable land) represent several advantages as compared to conventional energy crops. Algae, like certain land plants, have the ability to store large amounts of oils and microalgae have been demonstrated to be a source for biodiesel. The cell mass, or biomass, from algae can be used as a feedstock for fermentative organisms. De Schamphelaire et al. studied algae as a source of energy generation in a stand-alone, closed-loop system (De Schamphelaire, L.; Verstraete, W.; Laboratory of Microbial Ecology and Technology, Ghent University, Coupure Links 653, B-9000 Ghent, Belgium, 2009, Wiley Periodicals, Inc.). The system encompassed essentially a bioreactor for algal growth and an anaerobic digestion unit that converted the algae biomass to biogas and a microbial fuel cell to treat the effluent of the digester. As has been suggested by other researchers, nutrients generated during digestion can be recycled and, as necessary, be used for bacterial and algal growth. This system can then effectively convert sunlight to biogas and electricity and serves as a model to connect many energy conversion technologies to effectively create several forms of energy that can be used as biofuel for transportation or heat or be converted to electricity and used as input energy or sent for use in the electrical grid infrastructure to produce revenue. Algal productivities of 24-30 ton VS ha(−1) year(−1) were reached, while 0.5 N m$^3$ biogas could be produced kg(−1) algal VS. The system described resulted in a power plant with a potential capacity of about 9 kW ha(−1) of solar algal panel, with prospects of 23 kW ha(−1).

Diatoms.

Diatoms are unicellular algae that use photosynthetic systems A and C. Unicellular algae and diatoms can grow on sugar. Microalgae and diatoms can be grown in bioreactors photosynthetically or with sugar as feedstock. Diatoms can produce both starch and lipids. Starch can be used as sugar feedstock for organisms; lipids can be converted to biofuel. Diatoms, due to their silica containing cell wall can be used as an immobilized substrate for fermentative organisms that produce biofuels. Diatoms that produce starch photosynthetically can produce starch as feedstock for fermentative organisms with an amylase enzyme. *Clostridium* is a fermentative species that produces biobutanol and has been shown to be grown immobilized, in bioreactors on rice straw, which contains silica. Diatoms require a source of silica to grow.

Diatoms are microalgae of the classes Coscinodiscophyceae, Fragilariophyceae and Bacillariophyceae are particularly well suited to provide a high surface area matrix for immobilization of biofuel-producing microorganisms. Diatoms are widespread and can be found in the oceans, in freshwater, in soils and on damp surfaces. Most live pelagically in open water, although some live as surface films at the water-sediment interface (benthic), or even under damp atmospheric conditions. Although usually microscopic, some species of diatoms can reach up to 2 mm in length. This wide availability in nature allows for the easy selection of wild type species with optimum characteristics for use in the present invention.

Most diatoms are unicellular. Diatom cell walls are made from silica and contain two separate halves. Diatom silica shells (hydrated silicon dioxide) are called frustules. These frustules show a wide diversity in form, some quite beautiful and ornate, but usually consist of two asymmetrical sides with a split between them, hence the group name. The silica cell wall is synthesized intracellularly by the polymerization of silicic acid monomers, which is then extruded to the cell exterior and added to the wall forming the two halves that typically overlap one another like the two halves of a petri dish. In most species, when a diatom divides to produce two daughter cells, each cell keeps one of the two halves and grows a smaller half within it. As a result, after each division cycle the average size of diatom cells in the population gets smaller. Once such cells reach a certain minimum size, rather than simply divide vegetatively, they reverse this decline by forming an auxospore. This structure expands in size to give rise to a much larger cell, which then returns to size-diminishing divisions. In the process, a large surface area is created. Accommodating this growth cycle is important when immobilizing diatoms in a closed bioreactor system.

Diatoms are unique in that they can adjust their photosynthesis to maximal growth rate over broad wavelengths of light, control the growth rate of the matrix diatoms. Both marine and freshwater diatoms secrete extracellular polysaccharides. Generation of these polysaccharides apparently allows diatoms to live in a community setting as endobionts in sponges or with various proteobacteria. Moreover, the presence of certain bacteria strongly induced the carbohydrate secretion and biofilm formation.

Diatoms appropriate for use in the present invention may be wild type gathered from natural setting. Alternatively, wild type diatoms may undergo an artificial selection procedure in the laboratory. Wild type diatoms are collected then evolved under conditions known to one skilled in the art in the laboratory to produce valves of particular shapes and sizes. Selected strains suitable for use in the invention are then grown in chemostat cultures to mass produce stocks for seeding in a bioreactor.

Photosynthetic organisms use light to convert carbon dioxide and water into carbohydrate and oxygen. According to this invention, photosynthetic microorganisms, such as algae, are co-cultured with biofuel producing, non-photosynthetic microorganisms, such as yeast or *Clostridium*. The biofuel-producing non-photosynthetic microorganisms consume the carbohydrate produced by the photosynthetic microorganisms. This reduces or eliminates the need to provide extraneous carbohydrate to the biofuel-producing microorganisms. Furthermore, carbon dioxide produced by the biofuel producing microorganisms in the process of producing the biofuel, can be consumed by the photosynthetic microorganisms.

Microalgae, i.e., diatoms, are coated with a silica shell, called a frustule. Frustules provide a substrate on which certain biofuel-producing microorganisms can be immobilized. Immobilization enhances growth of certain microorganisms and their production of biofuel.

Microalgae are also known for the production of mono or polysaccharides. These sugars have been used as growth substrate for microorganisms in mono-culture. However, the secreted polysaccharide may also be used in multi-culture for use in the production of biofuels. The co-culture or co-localization of microorganisms in a bioreactor for the creation of a growth matrix allows the microorganisms to produce simultaneously or sequentially mono or polysaccharides for use in the production of biofuels and to produce solvent that allows liquid-liquid separation of biofuels from growth media.

Biofuel-producing microorganisms can be co-cultured with photosynthetic microorganisms that produce nutrients that feed the biofuel producing microorganisms. In certain embodiments, the photosynthetic microorganisms are microalgae, such as diatoms, that have silica shells, also called frustules. The biofuel producing microorganisms can grow on or in the spaces of the frustules as a matrix on which to grow. In other embodiments, the photosynthetic micoroorganisms, themselves, produce a biofuel, such as a lipid. The biofuels produced in the co-culture can be co-harvested.

Lipid-Producing Algae.

In another embodiment of the invention the primary biofuel-producing microorganisms are co-cultured with a secondary biofuel producing organism, e.g., an oil-producing algae. In this case, the primary biofuel-producing microorganisms are provided with an external carbon source. The algae can be, for example, a cyanobacterium and can include, for example, *Botryococcus braunii*, *Chlorella*, *Dunaliella tertiolecta*, *Gracilaria*, *Pleurochrysis carterae*, *Sargassum* or *Ulva*. These compositions can be co-harvested or isolated with the biofuels produced by the non-photosynthetic microorganisms.

4. Co-Culture

Co-culture of organisms can proceed as follows.

Co-Culture of Diatoms with Immobilizable, Alcohol-Producing Microorganisms

Co-culture can be performed in a bioreactor or in an environmentally open (e.g., open pond) configuration. The culture can be of any useful size, e.g., from 1 L to 1M L, 20 L to 1000 L.

Alternatively, in an open environment configuration, the culture can be spread over many hectares. The open pond can be an artificial pond, such as a raceway pond with hard or soft sides. Microalgae can be grown in the culture to a concentration of $10$-$10^6$/ml.

When the microalgae are established or as they are being established, the biofuel-producing organisms can be added to the culture. For example, yeast can be added in amounts of about $10^6$/ml and *Clostridium* can be added in added in amounts of about $10^7$-$10^{16}$/ml. Under these circumstances, the microorganisms will become immobilized on or within the silica frustules of the algae. Alternatively, microorganisms can be immobilized on another solid substrate, e.g., charcoal, bone char or synthetic beads.

In culture, the medium can include carbon, nitrogen, cofactors, vitamins, amino acids and other elements (e.g. trace metals) required for growth. Nutrients can be added to aid growth of both the algae and the fermentative organism. For example, the culture broth can contain calcium, magnesium, nucleotides, vitamins such as biotin and metals such as selenium and zinc. Diatoms require a source of silica to produce frustules. This can be supplied to the culture through, for example, a silica acid, rice straw or other silica based chemical.

Fermentative microorganisms produce alcohols anaerobically. Algae, on the other hand are aerobic. However, the microorganisms can produce alcohols in co-culture with algae under micro aerophilic conditions while also providing their fermentation by-product carbon dioxide which is a growth requirement for algae.

The culture can be exposed to light to aid growth of the algae. The light can be natural or artificial. May photon emitted diodes use very little energy that does not destroy the energy balance of the process or life cycle analysis. LEDs (Light Emitting Diodes) are an example of a low energy light source.

5. Co-Production of Biofuels

While non-photosynthetic organisms may be a primary source of biofuel in the systems of this invention, algae, including microalgae, produce lipids that are, themselves, useful as biofuels, such as biodiesels. Accordingly, lipid-producing microalgae can be co-cultured with an organism that produces a solvent in which the lipid is soluble. The two biofuels can be co-harvested. For example, fermentative organisms, such as *Clostridium*, produce butanol. Butanol can be used as a solvent to separate lipid produced by microalgae from water. Butanol can enhance the performance of biodiesel and does not need to be separated from the biodiesel. Alternatively, at high enough concentrations, lipid will also naturally separate from the broth, forming an organic phase separate from the aqueous phase. The biofuel produced by the co-cultivated microbe will partition into the organic phase to varying extents based on its hydrophobicity.

This separation method can be performed as follows. The broth, upon removal from the fermentor, is collected and allowed to settle and partition into two phases. If required butanol can be added to lipids to attain a concentration of 9% or greater and upon agitation the lipids will enter the butanol phase and separate from the water phase. Water can be decanted from the bottom of the vessel or butanol/lipid fraction can be decanted from the top.

Also, microalgae grown in such a system can be used as fertilizer and animal feed. Diatom silica can be used in nanotechnology. Carbon dioxide can be used in dry cleaning, dry ice production, in oil fields to displace liquid volumes in oil pumps and in the beverage industry for carbonation. Hydrogen can be used for fuel.

6. Biofuels

The harvested product of co-culture can be used as a biofuel. In the case of co-production of biofuels, e.g., oils and solvents, the harvested material can comprise the bio-oils mixed with the solvents (e.g., with butanol.) This mixture can be substantially free of water. Such mixtures also may contain the remnants of the microorganisms, e.g., the algae and/or the fermentative microorganisms in which they are grown. The biofuels also can be mixed with an oxygenation agent, such as ethanol or MBTE. The oils and lipids produced are useful as biodiesels.

EXAMPLES

Example 1

Co-Culture, or Co-Localization of microorganisms to simultaneously produce and utilize substrate for the production of biofuels.

The bioreactor contains microalgae or diatoms and/or bacteria, growing by photosynthesis or on another substrate. The microalgae produce polysaccharides or another end product that can be used as a substrate by a microorganism that produces an alcohol, alkene, alkane, lipid, polysaccharide or any end product useful as a biofuel.

The bioreactor may also contain microalgae, diatoms or bacteria that are not growing but can be used as a source of substrate for the growth or production by another microorganism of an alcohol, alkene, alkane, lipid, polysaccharide or any end product useful as a biofuel. The bacteria can be immobilized on the microalgae, diatoms or bacteria and be vectorially located for substrate utilization and biofuel production. Specifically, diatoms with silica containing fustula are the substrate producing matrix upon which biofuel producing bacteria can be grow either by utilizing substrate provided by the diatoms or through exogenous substrate being added.

Seawater and freshwater samples are collected in the Los Angeles, San Diego and Catalina Island areas of California. The sampling depth is between 1 and 10 m. Samples are diluted in series and growth was monitored. Subcultures of the dilution cultures are made in media as described by Schut et al. 1993, in filtered-autoclaved seawater (FAS), in synthetic seawater medium (MPM), and in sterilized lake water containing the following (in grams per liter of Milli Q-purified water (Millipore Corp., Bedford, Mass.): NaCl, 30.0; $MgCl_2.6H_2O$, 1.0; $Na_2SO_4$, 4.0; KCl, 0.70; $CaCl_2.2H_2O$, 0.15; $NH_4Cl$, 0.50; $NaHCO_3$, 0.20; KBr, 0.10; $SrCl_2.6H_2O$, 0.04; $H_3BO_3$, 0.025; KF (Sigma Chemical Company, St. Louis, Mo.), 0.001; morpholinepropanesulfonic acid (MOPS) buffer (Sigma) (pH 7.8), 2.09; $KH_2PO_4$, 0.27; trace element solution, 1.0 ml/liter; vitamin solution, 2.0 ml/liter; and a carbon source if necessary.

Selection of diatoms that produce polysaccharide is accomplished using standard media (Penna et al., *Journal of Plankton Research*, 1999, 21:9; 1681-1690) and protocols (Underwood, G. J. C. and Paterson, D. Al., *Limnol. Oceanogr.*, 1997, M(7)1243-1253) for the qualitative determination of the presence of diatomaceous starch by treating the supernatant of a diatom culture by staining for 30 min with a solution containing 5.7 mm iodine, 43.4 mM potassium iodide in 0.2 N HCl. Quantitative measurements of the carbohydrate are performed by homogenizing 0.5 ml samples in 80% ethanol. Starch is estimated as glucose released by amyloglucosidase treatment of the ethanol insoluble fraction. The ethanol soluble fraction is evaporated to dryness and the residues resuspended in water and assayed for hexose and sucrose content by HPLC or LC.

Diatoms are phototrophic and produce and secrete polysaccharideand that can be used by the seeded biofuels organism for growth. The biofuels organism can be a naturally occurring organism or an engineered organism.

A bioreactor of a given volume can operate singly or in parallel with other reactors. Appropriate bioreactor materials are selected (polypropylene or stainless steel for example) and a fluidized liquid bed of diatoms that produce polysaccharide is established using standard media and protocols.

Diatoms normally replicate about 8 times per day, so the fluidized bed is inoculated with circa 100 diatoms and at 8 days the density will be at about 104/ml. This bioreactor is then inoculated with the biofuels-producing organism at about 200/ml and the culture is allowed to grow heterotrophically, reaching high cell density of 108-1010/ml. Biofuel production is measured by mass spectroscopy or gas chromatography. This bioreactor is stable until contaminated or biofuel production stops. New organisms (as well as fresh nutrients, if needed) can be added through input ports, while dead organisms, depleted media and product can be removed through output ports.

Under appropriate culture conditions, the silica frustules of the diatoms are grown such that they have a ratio of about 1 diatom to $10^4$ biofuel producing organisms.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising co-culturing polysaccharide-producing photosynthetic wild type diatoms comprising frustules with polysaccharide-consuming, biofuel-producing, non-photosynthetic microorganisms, wherein the diatoms are grown with a source of silica and the non-photosynthetic microorganisms are immobilized on the frustules, wherein the non-photosynthetic microorganisms consume polysaccharide produced by the polysaccharide-producing photosynthetic wild type diatoms to produce a biofuel and wherein an external carbon source is not needed for production of the biofuel.

2. The method of claim 1 wherein the co-culturing comprises exposing the photosynthetic diatoms to light.

3. The method of claim 1 wherein the non-photosynthetic microorganisms are fermentative.

4. The method of claim 1 wherein the non-photosynthetic microorganisms comprise bacteria or fungi.

5. The method of claim 1 wherein the non-photosynthetic microorganisms comprise bacteria selected from *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Serratia, Shigella, Staphlococcus, Strepromyces, Synnecoccus*, and *Zymomonas*.

6. The method of claim 4 wherein the non-photosynthetic microorganisms comprise fungi selected from *Aspergillus, Candida, Chlamydomonas, Chrysosporium, Cryotococcus, Fusarium, Kluyveromyces, Neotyphodium, Neurospora, Penicillium, Pichia, Saccharomyces, Scenedesmun, Trichoderma* and *Xanthophyllomyces*.

7. The method of claim 4 wherein the non-photosynthetic microorganisms are genetically modified to increase biofuel production.

8. The method of claim 1 wherein the diatoms are selected from Coscinodiscophyceae, Fragilariophyceae and Bacillariophyceae.

9. The method of claim 1 wherein the non-photosynthetic microorganisms comprise yeast.

10. The method of claim 1 wherein the non-photosynthetic microorganisms comprise *Clostridium*.

11. The method of claim 1 wherein the biofuel is ethanol, propanol or butanol.

12. The method of claim 1 wherein the biofuel is an alcohol, an alkene, an alkane, a lipid or a polysaccharide.

13. The method of claim 1 wherein co-culturing comprises providing the diatoms with starch or sugar.

14. A co-culture of photosynthetic wild type diatoms comprising frustules and non-photosynthetic organisms, wherein the co-culture comprises a source of silica and the non-photosynthetic microorganisms are immobilized on the frustules, and wherein the photosynthetic diatoms produce polysaccharide and the non-photosynthetic microorganisms consume the produced polysaccharide and produce a biofuel and wherein an external carbon source is not needed for the production of the biofuel.

15. The co-culture of claim 14 wherein the non-photosynthetic microorganisms are fermentative.

16. The co-culture of claim 14 wherein the biofuel is ethanol, propanol or butanol.

17. The co-culture of claim 14 wherein the biofuel is an alcohol, an alkene, an alkane, a lipid or a polysaccharide.

18. The co-culture of claim 14 wherein the non-photosynthetic microorganisms comprise bacteria or fungi.

19. The co-culture of claim 14 wherein the non-photosynthetic microorganisms comprise yeast.

20. The co-culture of claim 14 wherein the non-photosynthetic microorganisms comprise *Clostridium*.

21. The co-culture of claim 14 further comprising starch or sugar.

* * * * *